US008068033B2

(12) United States Patent
Blokker et al.

(10) Patent No.: US 8,068,033 B2
(45) Date of Patent: Nov. 29, 2011

(54) METHOD OF DETECTING CONTAMINATION IN INDUSTRIAL PROCESS BOILER SYSTEMS

(75) Inventors: Peter Blokker, Heerhugowaard (NL); Peter D. Hicks, Aurora, IL (US)

(73) Assignee: Nalco Company, Naperville, IL (US)

( * ) Notice: Subject to any disclaimer, the term of this patent is extended or adjusted under 35 U.S.C. 154(b) by 275 days.

(21) Appl. No.: 12/262,581

(22) Filed: Oct. 31, 2008

(65) Prior Publication Data
US 2010/0109885 A1   May 6, 2010

(51) Int. Cl.
*G08B 21/00* (2006.01)
(52) U.S. Cl. .............. 340/603; 340/540; 340/286.01; 73/40.7; 422/11
(58) Field of Classification Search .......... 340/603, 340/540, 539.1, 286, 286.02, 286.01; 210/696, 210/748.13; 422/7; 73/40.7, 40, 40.5
See application file for complete search history.

(56) References Cited

U.S. PATENT DOCUMENTS

| | | | |
|---|---|---|---|
| 4,269,717 A | 5/1981 | Slovinsky | |
| 4,574,071 A | 3/1986 | DeSilva et al. | |
| 4,648,043 A | 3/1987 | O'Leary | |
| 4,775,005 A | 10/1988 | Beyer et al. | |
| 4,830,757 A | 5/1989 | Lynch et al. | |
| 5,236,845 A | 8/1993 | Pierce et al. | |
| 5,238,846 A | 8/1993 | Aucutt | |
| 5,243,297 A | 9/1993 | Perkins et al. | |
| 5,268,092 A | 12/1993 | Eden | |
| 5,332,494 A | 7/1994 | Eden et al. | |
| 5,342,510 A | 8/1994 | Eden et al. | |
| 5,348,664 A | 9/1994 | Kim et al. | |
| 5,422,014 A | 6/1995 | Allen et al. | |
| 5,470,484 A | 11/1995 | McNeel | |
| 5,747,342 A * | 5/1998 | Zupanovich | 436/55 |
| 5,855,791 A | 1/1999 | Hays et al. | |
| 6,068,012 A | 5/2000 | Beardwood et al. | |
| 6,077,445 A | 6/2000 | Ascolese | |
| 6,336,058 B1 * | 1/2002 | Fowee | 700/266 |
| 6,350,376 B1 | 2/2002 | Imaoka et al. | |
| 6,391,256 B1 | 5/2002 | Moon et al. | |
| 6,402,984 B1 | 6/2002 | Nakajima et al. | |
| 6,409,926 B1 | 6/2002 | Martin | |
| 6,418,958 B1 * | 7/2002 | Rossi et al. | 137/93 |
| 6,436,711 B1 | 8/2002 | Davis et al. | |
| 6,566,139 B2 | 5/2003 | Davis et al. | |

(Continued)

FOREIGN PATENT DOCUMENTS

JP   2003/254503   10/2003

OTHER PUBLICATIONS

Buecker B., "Water Treatment: The Continuing Battle Against FAC," Power Engineering, Pennwell Publishing Co., Tulsa, OK, pp. 32-34, vol. 106, No. 9, Sep. 1, 2002.

(Continued)

*Primary Examiner* — George Bugg
*Assistant Examiner* — Edny Labbees
(74) *Attorney, Agent, or Firm* — Edward O. Yonter; Michael B. Martin

(57) ABSTRACT

This invention provides a method for detecting contamination of a boiler condensate and/or a boiler feedwater in industrial fermentation processes. The method includes measuring an oxidation-reduction potential at one or more locations in the fermentation process with one or more devices capable of measuring oxidation-reduction potential at operating temperature and pressure. If the measured oxidation-reduction potential is not within an optimum range, an alarm is triggered.

16 Claims, 12 Drawing Sheets

U.S. PATENT DOCUMENTS

| | | | |
|---|---|---|---|
| 6,587,753 | B2 | 7/2003 | Fowee |
| 6,609,070 | B1 | 8/2003 | Lueck |
| 6,620,315 | B2 | 9/2003 | Martin |
| 6,813,532 | B2 | 11/2004 | Eryurek et al. |
| 7,141,175 | B2 | 11/2006 | Verma |
| 7,208,117 | B2 * | 4/2007 | Hays et al. .................. 422/3 |
| 2003/0004681 | A1 | 1/2003 | Fandrich et al. |
| 2006/0006122 | A1 | 1/2006 | Burns et al. |
| 2006/0169646 | A1 | 8/2006 | Andree et al. |
| 2006/0182651 | A1 | 8/2006 | Bailey, III et al. |
| 2008/0179179 | A1 | 7/2008 | Hicks et al. |
| 2008/0202553 | A1 | 8/2008 | Hicks et al. |

OTHER PUBLICATIONS

Dedekind et al., "Oxygenated Feedwater Treatment at the World's Largest Fossil Fired Power Plant —Beware the Pitfall," Power Plant Chemistry, vol. 3, No. 11, Nov. 2001.

Filer, "Power Plant Chemistry Measurement Advancements: Oxidation Reduction Potential," Ultrapure Water, Nov. 1998.

Haag, J. et al., "On-Line Measurement of Redox and Corrosion Potentials in Water for PWR Steam Generators," Kraftwerkstechnik, Kraftwerkstechnik GMbH, Essen, DE, pp. 236-241, vol. 70, No. 3, Mar. 1, 1990.

Niedrach, L. W., "Electrodes for Potential Measurements in Aqueous Systems at High Temperatures and Pressures,"Angewandte Chemie — International Edition in English, pp. 161-169, vol. 26, No. 3, Mar. 1987.

Uchino et al., "Study on the Practical Application of a Method for Corrosion Potential Measurement in a Water Quality Monitoring System used During Combined Water Treatment," PowerPlant Chemistry, pp. 511-517, vol. 3, No. 9, 2011.

* cited by examiner

METHOD OF DETECTING CONTAMINATION IN INDUSTRIAL PROCESS BOILER SYSTEMS

TECHNICAL FIELD

This invention relates generally to methods of detecting contamination of boiler condensate and/or boiler feedwater. More specifically, the invention relates to detecting and reducing contamination of boiler condensate and/or boiler feedwater in an industrial process. The invention has particular relevance to detecting contamination by wort or other contaminants in fermentation processes.

BACKGROUND

Boiler condensate and feedwater contamination is an undesirable and frequently occurring problem in the fermentation industry and other industries. These contaminants contribute to system inefficiencies, corrosion, deposition, and other system issues. Particularly with boiler systems or other steam-generating systems, such issues result in detrimental effects on heat transfer and reduced asset life. A common contaminant in fermentation processes, for example, is wort, which is the liquid extract obtained from the grain mashing process where one or more (including combinations) milled grains, for example, in beer brewing and whiskey distillation, are used as a fermentable substrate. Wort is a complex mixture that contains sugars that are fermented by brewing yeast to produce alcohol-containing product. Typical raw materials for its production include malted grain (e.g. barley) and water. In the beer brewing process it is sometimes referred to as hopped malt extract. Essentially this mixture is the basis for beer brewing and whiskey production processes.

Wort boiling is an essential step in beer brewing and whiskey production. It is a process by which hop components are extracted and transformed, including precipitation of proteins and conversion of dimethylsulfide to dimethylsulfoxide. During this process, the possibility exists, for example, of contaminating the boiler condensate due to direct steam contact with the product. Condensate contamination of the boiler feedwater might increase carryover from the boiler detrimentally resulting in organic acids in the steam and condensate system. Furthermore, steam purity is of the utmost importance to the industry due to possible contact of steam with the product and any contamination of the boiler or boiler water system compromises the entire operation.

Currently, measurement of wort contamination in condensate is performed with low frequency and using a well known laborious process. An example of such a system is disclosed in U.S. Pat. No. 5,238,846, titled "Method of Detecting the Presence of Sugar in Steam Generating Systems." The disclosed system includes detecting a calorimetric signal produced by exposing a grab sample with a reagent such as potassium permanganate and an acetate. Online measurement systems also exist; however, the devices used require high maintenance and are not considered robust.

There thus exists an industry need for improved methods of detecting wort and other contaminants in boiler condensate and feedwater. A particular need exists for low maintenance, reliable, and automated methods of such detection.

SUMMARY

This invention accordingly provides a method of detecting contamination in boiler systems, including boiler condensate and/or boiler feedwater in a industrial processes. Preferred industrial processes include those involving using, producing, or refining sugars and fermentation processes, such as beverage production (e.g., beer, whiskey) and industrial fermentation (e.g., ethanol, bioethanol). The method includes measuring an oxidation-reduction potential at one or more locations in the boiler condensate or boiler feedwater of the industrial process with one or more devices capable of measuring oxidation-reduction potential at operating temperature and pressure. If the measured oxidation-reduction potential is not within an optimum range, the method includes triggering an alarm or other indicator. Other indicators may include any type of signal or monitor that is operable, for example, to initiate a mechanism to stop or enable altering the operation of the industrial process. Such alterations will vary according to the particular indicator and application and will be determined by the operator or controller.

In an aspect, the method includes converting the measured oxidation-reduction potential into an input electrical signal capable of being transmitted to a controller and transmitting the input electrical signal to the controller. In a preferred aspect, the controller is operable to: (i) receive the transmitted input electrical signal; (ii) convert the received electrical signal into an input numerical value; (iii) analyze the input numerical value; (iv) generate an output numerical value: (v) convert the output numerical value into an output electrical signal; and (vi) transmit the output electrical signal.

In another aspect, the controller determines if the input numerical value is within an optimum range, and if the input numerical value is outside of the optimum range, the transmitted output electrical signal corresponding to the generated output numerical value triggers an alarm. In an embodiment, the method includes a mechanism to stop or alter the operation of the industrial process in the event of the alarm. In another embodiment, the method includes a mechanism to open or close one or more valves associated with the boiler condensate and/or a boiler feedwater or to cause other adjustments to the system as determined by the operator. One having ordinary skill in the art may determine the nature and degree of such adjustments.

In a further aspect, the invention includes a system for detecting contamination of boiler condensate and/or boiler feedwater in a beverage fermentation process. The system includes a boiler or other steam generator; a beverage fermentor; an interface that forms a thermodynamic connection between the beverage fermentor and a steam and/or condensate stream derived from said boiler or steam generator; a condensate return line; a condensate storage tank; a condensate dump valve; a boiler makeup water source; and one or more at temperature and pressure oxidation reduction potential measuring devices.

It is an advantage of the invention to provide a precise, sensitive, and efficient method of reducing contamination of boiler condensate and/or boiler feedwater in industrial processes by measuring only the oxidation-reduction potential at operating temperature and pressure.

It is another advantage of the invention to provide a method of detecting contamination by wort and other contaminants in boiler systems or steam-generating systems used in beverage fermentation processes.

Additional features and advantages are described herein, and will be apparent from, the following Detailed Description, Examples, and the Figures.

DETAILED DESCRIPTION

Figure 1:
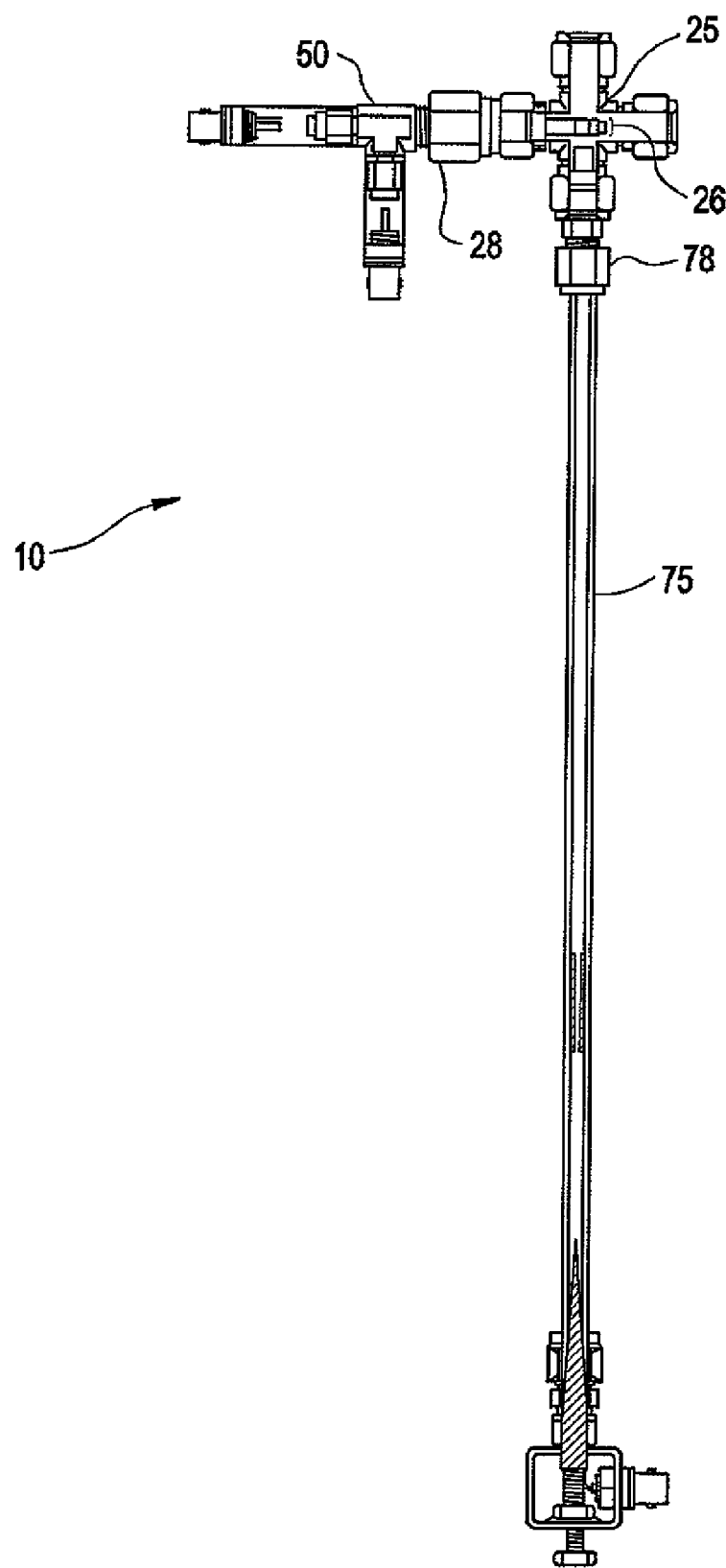
FIG. 1 is a side view of an embodiment of oxidation-reduction potential measuring device 10, shown with flow-through cell 25, union tee 50, and external pressure-balanced reference electrode assembly 75.

"Boiler" refers to any hot water system or steam generator having a temperature from about 37° C. up to about 370° C. The hot water system may operate at or below atmospheric pressure or a pressure up to about 3,000 psi. A typical system has a water temperature of about 90° C. to about 260° C. and pressures reaching as high as about 3,000 psi.

"Controller," "controller system," and similar terms refer to a manual operator or an electronic device having components such as a processor, memory device, cathode ray tube, liquid crystal display, plasma display, touch screen, or other monitor, and/or other components. In certain instances, the controller may be operable for integration with one or more application-specific integrated circuits, programs, computer-executable instructions, or algorithms, one or more hard-wired devices, and/or one or more mechanical devices. Some or all of the controller system functions may be at a central location, such as a network server, for communication over a local area network, wide area network, wireless network, internet connection, microwave link, infrared link, and the like. In addition, other components such as a signal conditioner or system monitor may be included to facilitate signal-processing algorithms.

In one embodiment, the control scheme is automated. In another embodiment, the control scheme is manual or semi-manual, where an operator interprets the ORP signals and determines whether changes to the system are necessary, such as chemistry dosage, condensate bypass, condensate dump valve(s), system shutdown, or other action. In an embodiment, the measured ORP signal is interpreted by a controller system that controls an amount of oxygen or oxygen scavenger to introduce to the system to keep the measured ORP within a determined range. In an embodiment, the controller system also interprets measured temperature to determine the amount of oxidant (e.g., oxygen) or reductant (e.g., oxygen scavenger) to add, if any, to the boiler feedwater. The temperature detector might also be used for information purposes, such as in alarm schemes and/or control schemes. It should be appreciated that the control scheme may incorporate pump limiters, alarming, intelligent control, and/or the like, based off further inputs, such as pH, dissolved oxygen levels, and other waste constituents.

"Fermentation process" refers to any process including the fermentation of one or more sugars into alcohol. These process include but are not limited to beer making processes, distillation process, industrial fermentation processes such as fuel ethanol or bioethanol.

"Hot water system" refers to any system where hot water is in contact with metallic surfaces in an industrial fermentation process. "Hot water" means water having a temperature from about 37° C. up to about 370° C. The hot water system may operate at or below atmospheric pressure or a pressure up to about 3,000 psi. A preferred hot water system is an industrial boiler system, which typically has a water temperature of about 90° C. to about 260° C. and pressures reaching as high as about 3,000 psi.

"ORP," "ORP measurement," "measured ORP," or like terms refer to oxidation-reduction potential measurements taken at operating temperature and pressure (unless otherwise noted). In an embodiment, the term encompasses concurrently measured and relayed temperature signals.

"ORP device" refers to any device capable of measuring oxidation-reduction potential. A preferred device is described in U.S. patent application Ser. Nos. 11/668,048 and 12/114,288, reproduced in part herein and incorporated by reference herein in their entirety, both titled "High Temperature and Pressure Oxidation-Reduction Potential Measuring and Monitoring Device for Hot Water Systems." Signals produced by the ORP device may be used in accordance with the embodiments described herein and optionally in conjunction with any suitable method including the methods disclosed in the following commonly owned U.S. patent applications (each incorporated herein in its entirety): "Method of Inhibiting Corrosion in Hot Water Systems," Ser. No. 11/403,420, now U.S. Pat. No. 7,635,449; "Method of Inhibiting Corrosion in Industrial Hot Water Systems by Monitoring and Controlling Oxidant/Reductant Feed Through a Nonlinear Control Algorithm," Ser. No. 11/692,542, now U.S. Pat. No. 7,666,312; "Method and Device for Creating and Analyzing an At Temperature and Pressure Oxidation-Reduction Potential Signature in Hot Water Systems for Preventing Corrosion," Ser. No. 11/782,246, now U.S. Pat. No. 7,955,853; "Method and Device for Preventing Corrosion in Hot Water Systems," Ser. No. 11/782,192; "Method and Device for Preventing Corrosion in Hot Water Systems Undergoing Intermittent Operations," Ser. No. 11/852,616, now U.S. Pat. No. 7,951,298; and "Method and Device for Cleanup and Deposit Removal from Internal Hot Water System Surfaces," Ser. No. 11/852,695, now U.S. Pat. No. 7,998,352.

"Wort" refers to the liquid obtained from the mashing process including fermentable sugars that are later converted by microorganisms into alcohol (typically ethanol).

Oxidation Reduction Potential Measuring Device

In a preferred aspect, the method of the invention incorporates a device for measuring and monitoring oxidation-reduction potential at operating temperature and pressure ("ORP"). In an embodiment, the device includes a flow-through cell, an electrode for sensing ORP in the system (sometimes referred to herein as "ORP probe"), a temperature detector, and a reference electrode. In a preferred embodiment, these components work in unison to measure and monitor ORP and temperature and to send these measured signals to a controller that determines feed rates of hot water system treatment chemicals, such as oxygen and/or oxygen scavengers. In a preferred embodiment, the measured potential (i.e., voltage difference) between the ORP probe within the flow-through cell and the reference electrode, preferably encased within an external pressure-balanced reference electrode assembly ("EPBRE"), indicates the ORP in a hot water system, such as an industrial boiler system.

In an embodiment, the device includes a flow-through cell having a plurality of ports including a first port, a second port, an inflow port, and an outflow port. In an embodiment, the device includes an ORP probe associated with the first port and having a connection to relay information to a controller. In an embodiment, the device further includes a temperature-dependent resistance sensor (sometimes referred to as "resistance temperature detector") associated with the first port and having a connection extending from the flow-through cell to a temperature detector electrical connection operable to relay information to a controller.

In one embodiment, the device also includes an external pressure-balanced reference electrode assembly associated with the second port. The assembly includes a porous frit on a first end of the assembly inside of the flow-through cell and a tube including an electrolyte solution and extending from the first end of the assembly to a second end of the assembly. The second end of the assembly is attached to a silver/silver chloride half-cell reference electrode having an electrical connection and operable to relay information to the controller.

In an embodiment, the device includes an ORP probe associated with the first port and having a first end and a second end. A platinum (or other noble metal) band is attached to the first end and resides within the flow-through cell. A corrosion-resistant wire (e.g., platinum) extends from the platinum band on the first end to the second end. The second end includes an electrical connection operable to relay information to a controller.

It should be understood that the disclosed device is capable of measuring and monitoring ORP and temperature in any still or flowing aqueous system or stream, but is primarily outfitted for the extreme conditions found in an operating hot water system or industrial boiler system, such as those used in industrial fermentation processes. Temperatures may reach as high as about 260° C. and pressures may reach as high as about 3000 psi in such systems. In an embodiment, the ORP and temperature signals are continuously monitored. Alternatively, the signals may be monitored according to a timetable or intermittently monitored.

The measured ORP signal occurs naturally in the aqueous environment of the hot water system due to polarization of the ORP probe. Instead of using current to impress voltage, the specially designed ORP measuring and monitoring device allows passive measurement of ORP using free-floating potentials in the system. A suitable voltage signal-interpreting unit, such as a high input impedance voltmeter or other device, is typically needed to interpret or convert such potentials or voltage signals to a readable format. In a preferred embodiment, when installed vertically, the base of the EPBRE (i.e., the site of the multi-fitting housing, described in more detail below) is at ambient temperature, regardless of the system temperature; however the base remains at system pressure. In alternative embodiments, the base of the EPBRE may be in any position relative to the flow-through cell and its temperature may be at any level between ambient and system temperature, depending on the particular application.

Terms such as "coupler," "fitting," "nut," and the like as used herein are not intended to be differentiating, rather they are intended to generally describe and represent a similar type of fastener mechanism. Such terms are used for convenience and not due to a structural or functional limitation. Any suitable mechanism of attachment may be used for described couplers, fittings, and other fasteners or connectors. Typically, the attachment mechanisms are designed to withstand the temperatures and pressures encountered in a hot water system. To aid in sealing any of the couplers, fittings, etc. herein described, sealing agents such as polytetrafluoroethylene ("PTFE") tape, liquid PTFE, plumber's putty, silicone, or other suitable sealing agent may be used. Further, reference to a fitting as "high-pressure" is not intended to distinguish that fitting from others herein described, as each fitting is chosen depending on the particular hot water system characteristics.

Representative, nonlimiting examples of fittings, couplers, connectors, junctions, nuts, bolts, and the like herein described include NPT fittings, quick release NPT fittings, AN-style fittings, flared fittings, compression-type fittings (such as those utilizing ferrules), or any other suitable couplers, adaptors, fittings, or fasteners. Welding, brazing, gluing (e.g., cyanoacrylate, resin, or other suitable adhesive), or other type of permanent or semi-permanent attachment is also contemplated for some applications. Any suitable size, shape, material, etc. of the coupler, fitting, connector, adaptor, or junction may be used and is determined based upon the characteristics and demands of the particular application.

Certain electrical connections, such as cathodic and anodic connections, are provided herein in accordance with embodiments of the invention. In an embodiment, an ORP probe includes an anodic connection and a reference electrode includes a cathodic connection. Such connections are so named for convenience and by convention. In alternative embodiments, the poles for these connections may be transposed or switched, where, for example, the reference electrode is the anodic connection and ORP probe is the cathodic connection.

In one embodiment, all described electrical interfaces or connections associated with those interfaces (i.e., connections for the ORP probe, reference electrode, temperature detector) include a BNC-type connector. Alternatively, the connections may include other types of RF connectors, TNC-type connectors, banana plugs, crimp connectors, other types of electrical connectors, soldered connections, direct wire, or any other suitable electrical interface or connection.

Referring to FIGS. 1 to 8, preferred embodiments of the ORP measurement and monitoring device (hereinafter sometimes referred to as the "ORP device") are illustrated and explained, where like numerals denote like components. In FIG. 1, an embodiment of ORP device 10 is shown with flow-through cell 25, sensor 26, union tee 50, and external pressure-balanced reference electrode assembly 75. The flow-through cell ("FTC") typically is the "foundation" of the ORP device to which other components are connected, including the temperature detector, sensor, and external pressure-balanced reference electrode assembly ("EPBRE"). In alternative embodiments, however, other components may be separate from the FTC and thus not directly connected to the FTC. In this embodiment, coupler 28 connects the FTC to the union tee and fitting 78 connects the FTC to the EPBRE.

Preferred fasteners include ¼ or ⅜ inch NPT fittings for coupler 28 and fitting 78. These connectors may be any suitable size and the examples herein are not intended to be limiting. For instance, a ⅜ inch female adaptor may be used for coupler 28, such as Part No. SS-6-TA-7-4, and reducing union Part No. SS-400-R-6BT may be used for fitting 78 (both available from, for example, Swagelok Company in Solon, Ohio). In this embodiment, the EPBRE is illustrated "hanging" underneath and vertically with respect to the FTC. Such a vertical configuration is one embodiment and it should be appreciated that the EPBRE may be positioned at any angle relative to the FTC according to alternative embodiments. Preferably, the ORP device is installed so that the EPBRE points directly downward and towards the ground. This downward position maintains the EPBRE base at ambient temperature and ensures against bubble formation within the electrolyte solution (explained below). If the base of the EPBRE is not at ambient temperature, corrections are typically made to adjust for thermal potentials within the electrode. The temperature of the base of the EPBRE may be determined using any suitable temperature-sensing device.

Figure 2:
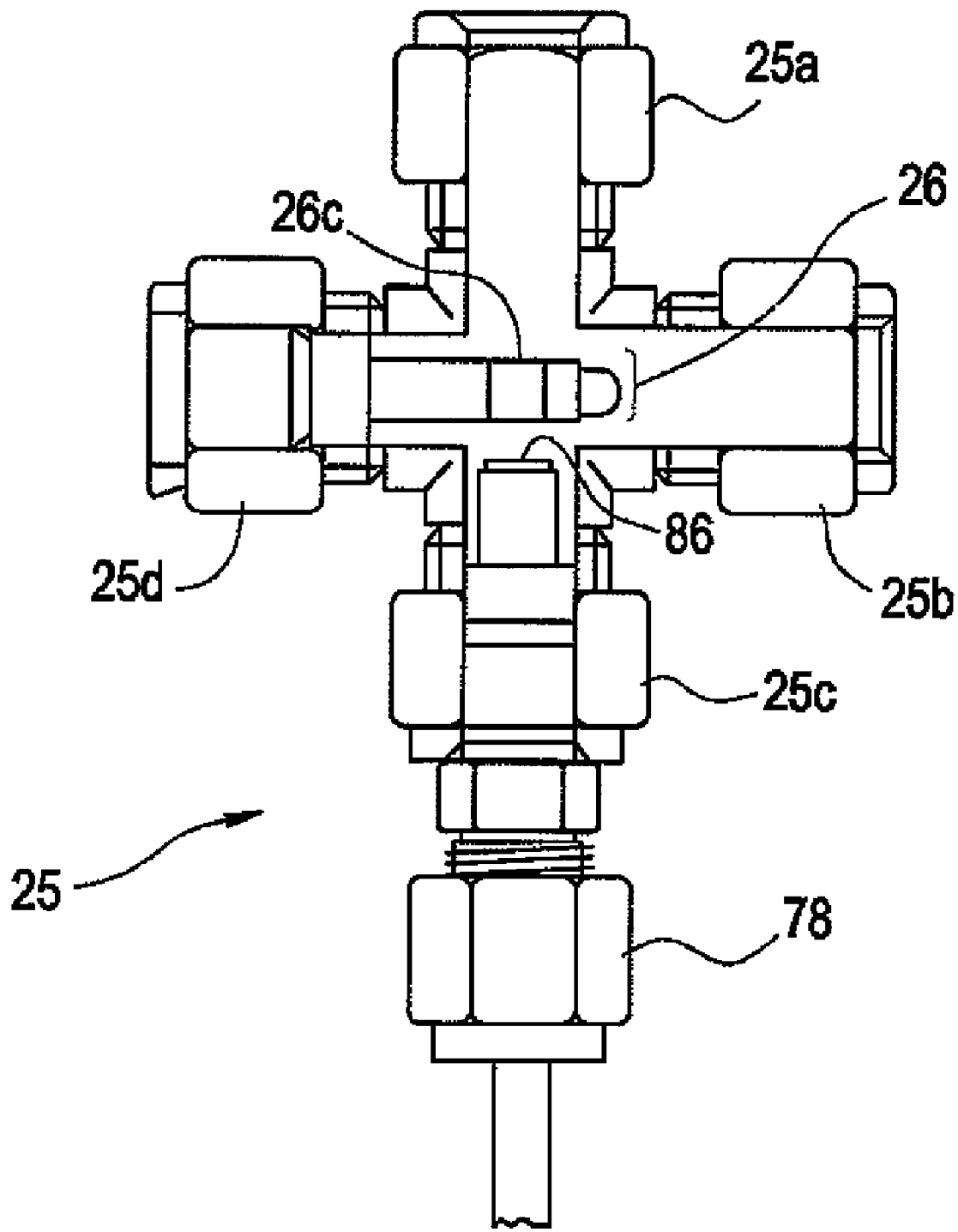
FIG. 2 is a schematic diagram of an embodiment of flow-through cell 25 having ports 25a, 25b, 25c, and 25d, sensor 26, high-pressure fitting 78, and coupler 28.

FIG. 2 illustrates a preferred embodiment of FTC 25. Though this schematic illustrates an embodiment having four ports, 25a to 25d, it is envisioned that the FTC may have additional ports such as for attaching or adding other components or for accommodating additional inflows and/or outflows. Some or all ports may be internally or externally connected or separate. An example of a preferred four-port FTC is ⅜ inch tube fitting, union cross Part No. SS-600-4 (available from, for example, Swagelok Company in Solon, Ohio). In a preferred embodiment, the FTC is constructed of the ⅜ inch stainless steel cross and includes a bored-through configuration having 4 connected ports. It is contemplated that the bore size and other dimensions of the FTC may be chosen to accommodate any possible flowrate, as determined for each application. Preferred and typical flowrates include from about 50 ml/min to about 1,000 ml/min. More preferred flowrates are from about 100 ml/min to about 500 ml/min.

As shown in FIG. 2, inflow port 25b accommodates a water inflow from the hot water system and outflow port 25a directs the water back into the system or into a waste stream. In alternative embodiments, valves or other flow control devices may be used to control inflow and outflow into the FTC. One embodiment of such a flow control system is illustrated and explained in FIG. 9 below. It should be appreciated that the invention may include more than one inflow and/or outflow port, which may be configured to work in unison, independently controllable, or configured and operated in any suitable fashion. Port 25c in this embodiment includes high-pressure fitting 78 that connects the FTC to the EPBRE.

In an embodiment, sensor 26 is associated with the FTC and protrudes into near the center of the FTC. In one embodiment, the sensor includes an ORP probe. In another embodiment, the sensor includes a temperature detector. In a further embodiment, the sensor includes both the ORP probe and the temperature detector. In an embodiment, the temperature detector is a temperature-dependent resistance sensor, described in more detail below. When the water inflow contacts the ORP probe, for example, an ORP signal is produced between the ORP probe and the reference electrode that is relayed to the control system. The ORP probe is typically positioned in relation to porous frit 86, as explained in more detail below. Preferred materials for the porous frit include ceramic or electroceramic materials, such as zirconia, polymeric materials, the like, or any other suitable porous material. It is preferred that the porous frit be inert to hot water system processes and ORP signal measurement.

Figure 3:
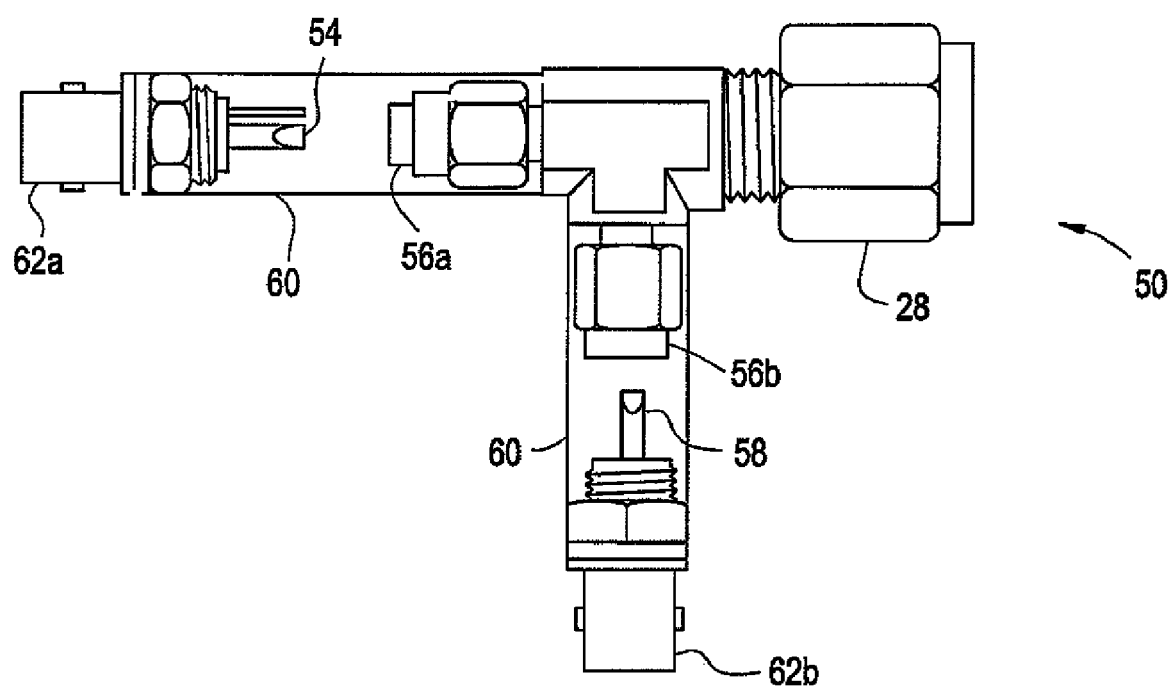
FIG. 3 is a schematic diagram of an embodiment of union tee 50 including coupler 28, temperature detector electrical connection 54, ferrules 56a and 56b, oxidation-reduction potential probe connection 58, L-bracket 60, and BNC connectors 62a and 62b.

In FIG. 3, an embodiment of union tee 50 is shown including coupler 28, temperature detector electrical connection 54, ferrules 56a and 56b, ORP probe connection 58, L-bracket 60, and BNC connectors 62a and 62b. Coupler 28 connects the FTC at port 25d to the union tee. A preferred connector for coupler 28 is Part No. SS-6-TA-7-4 (available from, for example, Swagelok Company in Solon, Ohio). In a preferred embodiment, the union tee includes two ⅛ inch tube connectors having a ¼ inch NPT connector on the remaining end that connects to coupler 28. In an embodiment, the union tee is mounted on or attached to the L-bracket or other stabilizing device or attachment. In alternative embodiments, the union tee may have other suitably sized fittings, which may be standard, metric, small, large, or any suitable configuration. One end of the union tee is connected to the flow-through cell according to an embodiment. Connected at the other two ends of the union tee are the temperature detector electrical connection and the ORP probe connection. Though any suitable union tee may be used, a preferred union tee is Part No. SS-200-3-4TMT (available from, for example, Swagelok Company in Solon, Ohio).

Figure 4:
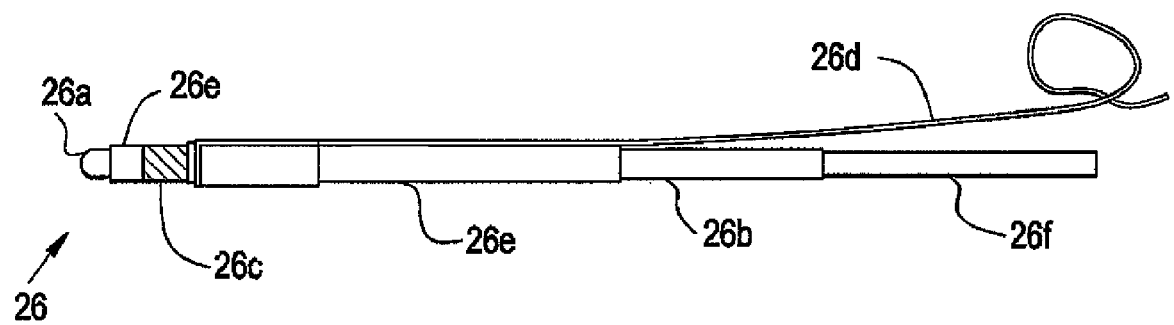
FIG. 4 illustrates an embodiment of sensor 26 having temperature detector 26a, insulating heat shrink 26b, noble metal band 26c, wire 26d, anchoring heat shrink 26e, and tube 26f.

FIG. 4 depicts an embodiment of sensor 26 having temperature detector 26a (at the "tip" of the sensor), insulating heat shrink 26b, noble metal band 26c, wire 26d, anchoring heat shrink 26e, and tube 26f. In this embodiment, tube 26f is a one end closed stainless steel tube having an outside diameter of about ⅛ inch and extending from about the center of the flow-through cell into the union tee. It should be appreciated that the tube may be of any suitable diameter, as determined for each application. The tube functions to provide support for noble metal band 26c ("band") and may include any corrosion-resistant material, such as stainless steel of any suitable composition, aluminum, other metals and plastics, and combinations thereof. In a preferred embodiment, the band functions as a passive ORP sensor. The ORP of the sample water is measured on the passive surface relative to the reference electrode. The band is located, in an embodiment, near the center of the FTC (as explained above for FIG. 2) and is in direct contact with the aqueous stream.

In a preferred embodiment, the temperature detector is a temperature-dependent resistance sensor (such as a PT100, PT200, PT1000, CU10, NI120). In one embodiment, the temperature-dependent resistance sensor is encased within tube 26f and is not directly exposed to the aqueous stream. The temperature detector may also include a standard thermocouple (such as type J, K, T, or E) or other temperature-sensing device according to alternative embodiments. In an embodiment, sensor 26 includes both an ORP probe having a noble metal band and a temperature detector, which are combined into one integrated component. In one embodiment, the sensor includes a plurality of wires. For example, wire 26d may transmit the ORP signal and one or more other wires transmit temperature signal(s).

Figure 5:
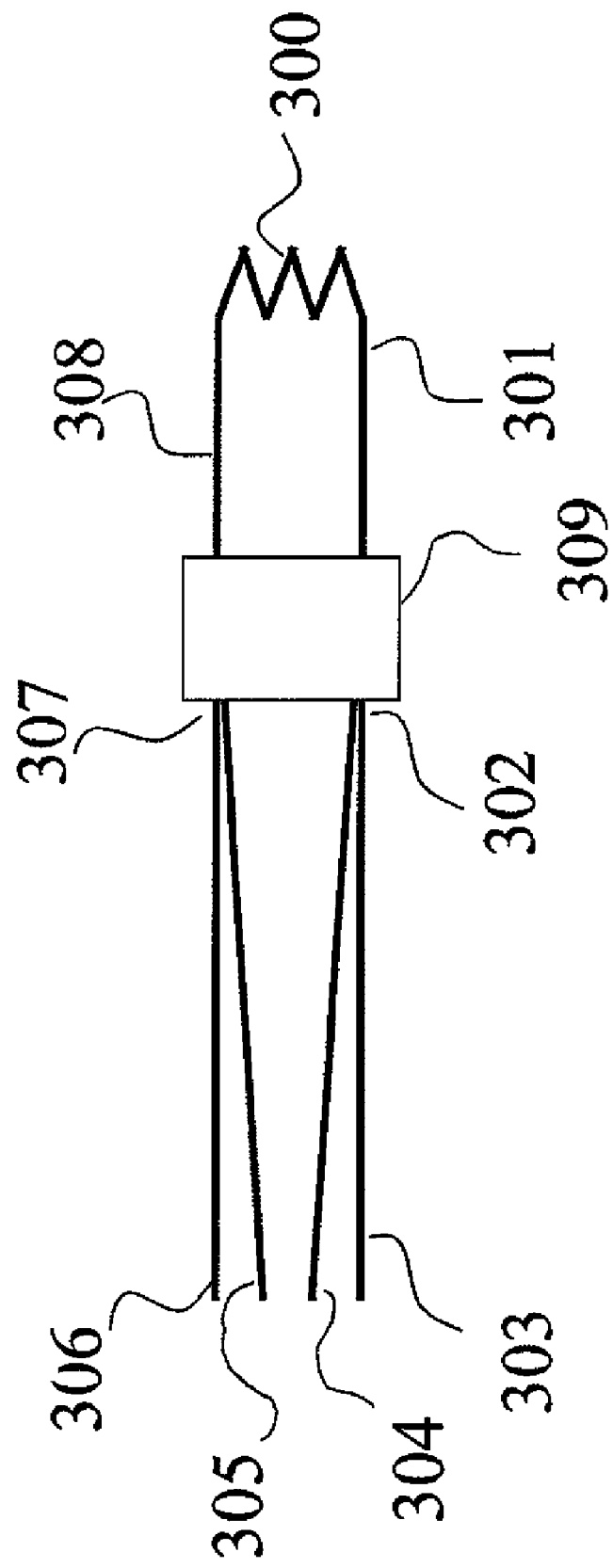
FIG. 5 depicts a preferred embodiment of the resistance temperature detector 300 including two positive electrical leads 303 and 304 and two negative electrical leads 305 and 306.

In a more preferred embodiment, the temperature detector includes a plurality of wires or electrical leads. Such a configuration overcomes errors introduced as a result of the inherent resistance of the electrical leads. FIG. 5 illustrates a resistance temperature detector with two positive electrical leads 303 and 304 and two negative electrical leads 305 and

306. Fitting 309 corresponds to BNC fitting 62a in FIG. 3. To ascertain temperature in the area about resistor 300, voltage (or current) is applied across the resistor, with the resulting voltage drop being used to determine temperature (as known in the art for resistance-based temperature detectors). Any deviations from the known voltage are related to changes in the resistance of resistor 300 as a function of temperature.

A configuration as in FIG. 5, where the resistance temperature detector includes a plurality of positive electrical leads and a plurality of negative electrical leads allows a user or controller to factor out inherent measurement errors. For example, measuring the voltage drop between positive electrical leads 303 and 304 and negative electrical leads 305 and 306 allows the controller to more accurately measure the voltage drop across any pair of positive/negative electrical leads. The resultant measurement provides an accurate reading of the voltage drop across resistor 300, which in turn provides a more accurate temperature reading.

In the embodiment depicted in FIG. 5, resistor 300 corresponds to temperature sensor 26a of FIG. 4. Positive electrical leads 303 and 304 connect to fitting 309 at point 302 and negative electrical leads 305 and 306 connect to fitting 309 at point 307. Positive lead 301 connects point 309 to resistor 300 and negative lead 308 connects point 307 to resistor 300.

Alternative configurations for the temperature detector may include one, two, or more temperature detectors used either independently or in conjunction with one another. For example, if two temperature detectors are employed, one detector may be used to monitor temperature near the FTC while the other monitors the temperature near the reference electrode. Such configurations allow the user or operator of the ORP device to evaluate and calculate thermal potentials that might exist along the length of the EPBRE. This data would then be used to correct and deconvolute ORP values with respect to temperature differentials and potentials.

Figure 6:
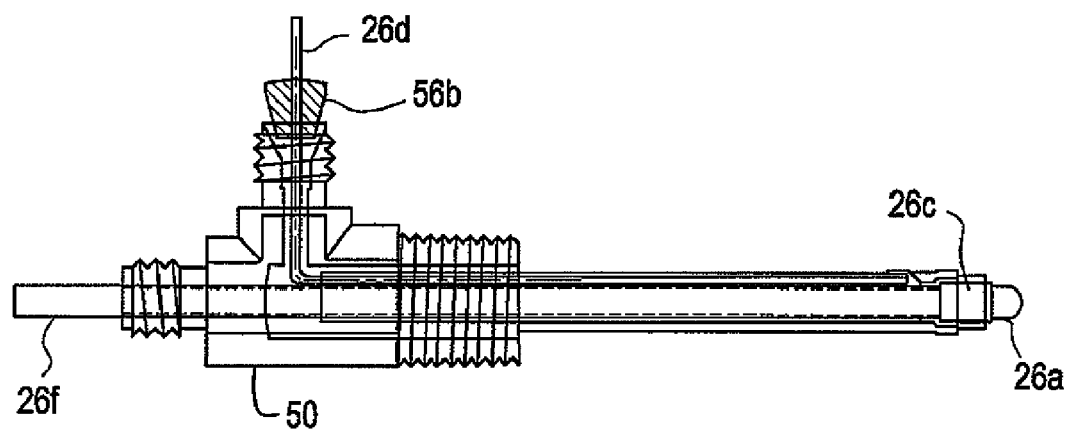
FIG. 6 is a cutaway view of the spatial relationship between several described components, including temperature detector 26a, insulating heat shrink 26b, noble metal band 26c, wire 26d, anchoring heat shrink 26e, tube 26f, union tee 50, and ferrule 56b, according to a preferred embodiment.

The wire and band may include any noble metal, such as gold, silver, tantalum, platinum, rhodium, copper, and/or the like. Platinum is preferred. In an embodiment, any wire herein described may include an insulating material, such as plastic or PTFE, wrapped around such wire. Wire 26d is connected to the band and transmits an electrical signal to anodic connection 58. In an embodiment, other wires (not shown) transmit an electrical signal to temperature detector electrical connection 54 from an "active" portion of a resistance temperature detector that resides within the closed end of the tube at tip 26a. FIG. 6 illustrates a detailed cutaway view of the spatial relationship between several described components according to a preferred embodiment. In one embodiment, the tail end of sensor 26 protrudes through the union tee and into the space on the opposite side of the union tee from the FTC (as shown in FIG. 6). In this embodiment, the active portion of the temperature-dependent resistance sensor is located within the tube 26f at tip 26a.

Figure 7:
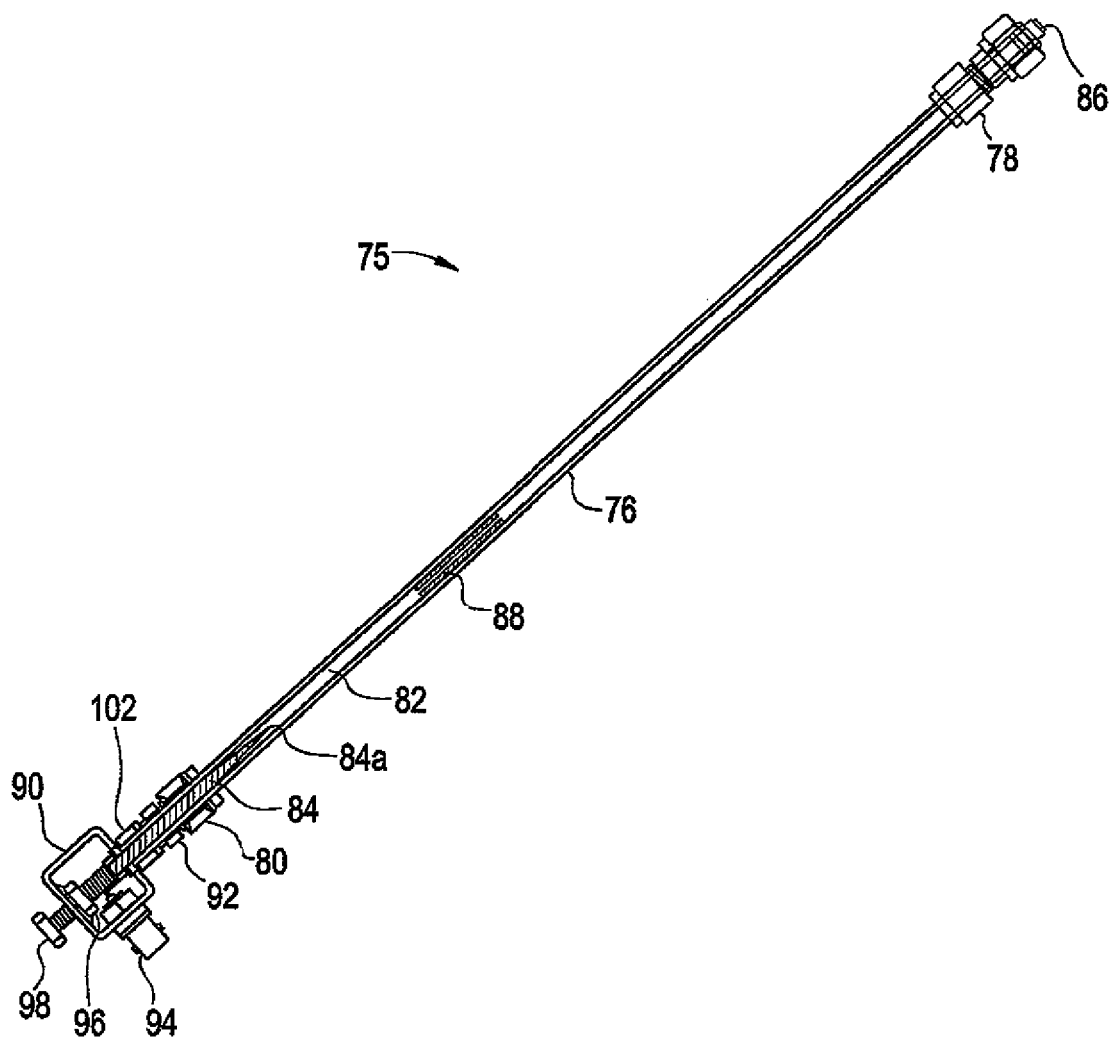
FIG. 7 depicts an embodiment of external pressure-balanced reference electrode assembly 75 including external tube 76, high-pressure fitting 78, high-pressure connector 80, internal tube 82, reference electrode 84, porous frit 86, insert 88, multi-fitting housing 90, reducing union 92, BNC connector 94, locking nut 96, bolt 98, and fastener 102.

A preferred embodiment of the reference electrode includes EPBRE 75, which acts to encase and thermally isolate the reference electrode. Illustrated in FIG. 7 is an embodiment of EPBRE 75 including external tube 76, high-pressure fitting 78, high-pressure connector 80, internal tube 82, reference electrode 84, porous frit 86, insert 88, multi-fitting housing 90, reducing union 92, BNC connector 94, locking nut 96, bolt 98, and fastener 102. The external tube in this embodiment is a ⅛ to ½ inch inner diameter stainless steel tube and houses the internal tube. In an embodiment, the EPBRE includes one or more inserts 88, which function to allow the internal tube to be separated to refresh, check, replace, refurbish, etc. the electrolyte solution, as explained in more detail below.

It should be appreciated that the external tube, the internal tube, and insert may be made of any suitable material of any suitable size, such as stainless steel, aluminum, PTFE, plastic, other suitable polymeric material, or other suitable metal. Preferably, the external tube is stainless steel (such as ¼ inch outside diameter 316 stainless steel tubing available from, for example, McMaster-Carr in Elmhurst, Ill.) and the internal tube is PTFE having a tight fit with the external tube. In this example, external tube 76 is about 5 to about 25 inches long. Preferably, the external tube is about 10 to about 20 inches in length. The length of the external tube acts to thermally isolate the reference electrode (within the EPBRE) from the hot water system while maintaining about equal pressure between the hot water system and the reference electrode. It is made from any suitable tubing material, and any suitable diameter or length may be used.

Figure 8:
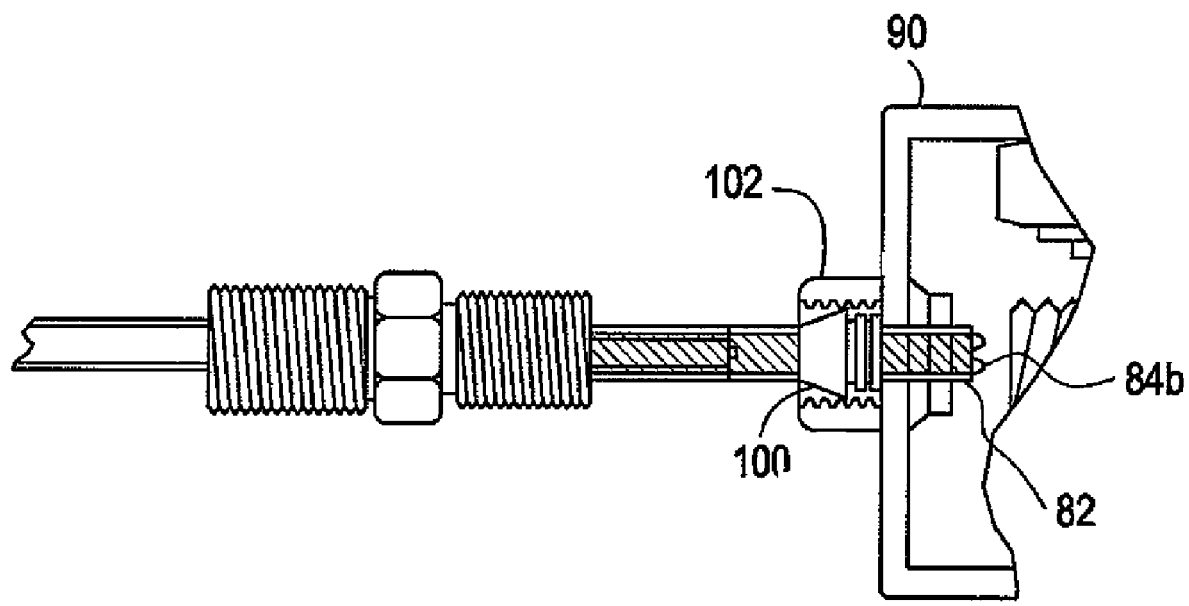
FIG. 8 shows an embodiment of multi-fitting housing 90 having sealed junction 100, fastener 102, internal tube 82, and reference electrode connection 84b.

An embodiment for the multi-fitting housing or "base" of the EPBRE is illustrated in FIG. 8, which includes sealed junction 100, fastener 102, and reference electrode connection 84b of the reference electrode. The sealed junction preferably includes a non-metallic, multi-ferrule material. In this embodiment, the sealing material in the sealed junction comprises 3 separate PTFE ferrules secured with a 3/16 inch nut to the multi-fitting housing. An example of such a ferrule "assembly" includes Part No. T-303 and T-304 (available from, for example, Swagelok Company in Solon, Ohio). In other embodiments, different types of seals and sealing materials may be used for the sealed junction. For example, the sealing material may include a gasket, elastomer, silicone, cork, flared fitting, rubber sleeve, o-ring, or any suitable seal or sealing material. In this embodiment, the ferrules function to place pressure on reference electrode 84, which is encased by the internal tube. Connector 80 is attached to reducing union 92 by, for example, standard stainless steel ferrules. The ferrules place pressure on the external tube thus holding it in place and providing a pressure-safe boundary.

The reference electrode is preferably about 2.5 to about 3.5 inches long and is tapered from tip 84a to sealed junction 100. In an embodiment, the reference electrode diameter remains constant from the sealed junction to reference electrode connection 84b. The reference electrode connection end is typically about 0.125 inches in diameter and the tip is typically about 0.01 inches in diameter. These diameters may be any suitable diameter according to alternative embodiments. The reference electrode (preferably a silver/silver chloride half-cell, where the tapered rod-shaped electrode includes silver with a silver chloride coating) extends from inside the internal tube (i.e., the tip is in contact with the electrolyte filling solution) to the end of the external tube and contacts the reference electrode connection. The reference electrode connection end includes a notch to accommodate a wire connecting the reference electrode to BNC connector 94 operable to transmit the electrical signal from the reference electrode to a receiver or controller, according to an embodiment. Bolt 98 acts to prevent the reference electrode from ejecting under system pressure and is typically made from any electrically isolating material, such as nylon, PVC, or other plastic.

Though a multitude of methods for assembling the described ORP device exist, an exemplary method includes boring through union tee 50 with a ⅛ inch (or any size that matches the size of tube 26f) drill to allow insertion of tube 26f through the union tee. L-bracket 60 is then attached (e.g., welded) to the union tee and coupler 28 is attached to the FTC side of the union tee. In a subsequent step, the coupler will be used to affix the union tee to one of the ports, such as port 25c, on the FTC.

Forming the ORP probe (in an embodiment, noble metal band 26c) includes using a band (preferably platinum) having width of about 1/16 to about 1/2 inch preferably about 1/4 inch) and a diameter large enough to fit around tube 26f. Insulating heat shrink 26b is shrunk on tube 26f, leaving about 1/8 inch of the tube's closed-end exposed. A small portion of the band is then cut out and the now "C-shaped" band is tightly wrapped or folded around the insulating heat shrink. The cutaway portion or seam of the band should ultimately face away from porous frit 86 upon final assembly. One end of wire 26d is placed between the insulating heat shrink and the band, which is then crimped onto the insulating heat shrink. This crimping secures wire 26d between the insulating heat shrink and the band. The wire is typically further secured to the band through welding, soldering, etc. The wire is typically about 0.001 to about 0.01 inches in diameter and has a length (typically about 2.5 to about 4.5 inches) long enough to reach ORP probe connection 58.

In an embodiment, a temperature-dependent resistance sensor resides within tube 26f. For example, a 4-wire temperature-dependent resistance sensor is transformed into a 2-wire connector and linked to BNC temperature detector electrical connection 54. A small amount of heat shrink or other stabilizing material may be placed on the temperature-dependent resistance sensor to provide support and electrical isolation. The resistance sensor is then inserted into open end of tube 26f up to the closed-end of the tube. As the temperature of the outside surface of the tube changes relative to the aqueous stream, the heat change triggers resistance changes in the temperature-dependent resistance sensor, which, in turn, is sensed by the controller system.

Thus, tube 26f internally houses or encases a temperature-dependent resistance sensor and the ORP probe including noble metal band 26c resides on its outer surface, according to an embodiment. The tube is typically from about 3.5 to about 5 inches; however, any suitable length will work. Upon cutting the tube to length, and placing insulating heat shrink on a portion of the tube, the wire and band are secured in place. The insulating heat shrink may either cover nearly the entire tube or only partially cover the tube thus leaving a portion of each end of the tube exposed. For example, a small portion of the closed-end, such as 1/8 inch, and a slightly larger portion of the open end, such as about 1/2 inch to about 1 inch, may be exposed.

Another component, anchoring heat shrink 26e, acts to help hold the band and wire in place. In an embodiment, a first portion of the anchoring heat shrink is placed in front of the band (i.e., between the band and the closed-end tip of the tube) and a second portion of the anchoring heat shrink is placed on the other side of the band. The second portion of the anchoring heat shrink slightly overlaps the band and functions to further secure the band and the wire to tube 26f.

The assembled tube is then slid into the union tee and locked in place as follows. The wire extending from the band is inserted through the bottom portion of the union tee towards ferrule 56b and the end of the tube (also having the end of the temperature-dependent resistance sensor) is inserted into the union tee towards ferrule 56a. The ferrules are then locked and sealed. The wires extending from the ORP probe and temperature-dependent resistance sensor are then affixed to the BNC connectors, preferably by soldering. Electrical checks should be performed to ensure continuity between the band and the BNC fitting and to ensure the absence of conductivity between the band or wire and the rest of the assembly.

In one embodiment, multi-fitting housing 90 is typically made from stainless steel (other suitable metals, plastics, etc. are also contemplated) and has two main functions. The first function is to house the reference electrode electrical connection and the second function is to provide structural support to prevent reference electrode 84 from ejecting under system pressure. A reducing union nut is welded or otherwise attached to a first fitting of the multi-fitting housing. Locking nut 96 is secured to the inside of a second fitting of the multi-fitting housing. Bolt 98 is inserted into the locking nut to ensure the reference electrode is pressure-safe. BNC connector 94 attaches to a third fitting of the multi-fitting housing. Each of the above components may be secured using any suitable means, including welding, soldering, epoxying, and the like.

Assembling the EPBRE includes preparing the reference electrode, which has a taper extending across a length of the reference electrode, as explained above. The tapered portion of the reference electrode resides in the electrolyte solution. The reference electrode preferably is electro-chloridized by dipping it in about a 1 molar hydrochloric acid solution and passing about a 3.5 milliamp current across the reference electrode and a counter electrode for about 4 hours.

An exemplary method of electro-chloridizing the reference electrode includes setting up in a 1-liter glass cell with about 1 liter of 1 molar hydrochloric acid solution. Two carbon counter electrodes connected together serve as the counter electrode (to be connected to a potentiostat counter electrode lead). The reference electrode is preferably a silver rod as described above, which is suspended in the center of the glass cell. Both counter electrodes are 180 degrees apart at opposite edges of the glass cell. A typical potentiostat setup is: Current range 100 mA, mode galvanostat; Set scan setup: I1 0 A; delay 1 to 10 s; scan I1 mA/s; 12-8.3 mA (feed in as 0.083-mA); delay 2 6500; scan 2 10 s; I3 0 A. Electrodes may be stored in a 0.1N KCl solution after electro-chlorodizing.

In an embodiment, the internal tube includes one insert 88 that separates the internal tube into an upper portion and a base portion (and by functionality, also may separate the external tube into two portions). The upper portion is attached to one of the ports on the FTC and the base portion is attached to the base of the EPBRE. The two portions are connected using the insert. Such separability allows servicing the electrolyte solution within the internal tube.

To form the upper portion, a section of PTFE heat shrink tubing (shrinks to about 1/8 inch outside diameter) about 12 inches long is heated to 345° C. in a kiln and cooled. Typically, a thin stainless steel (or other suitable material) tube placed inside of the PTFE tubing provides structural support during the heating and cooling process. The support tube is removed after cooling. Porous frit 86 has, in this example, an outside diameter of about 1/8 inch, a length of about 1/2 inch, and a porosity of about 10% to about 20%. One end of the shrunk tubing is trimmed to achieve a length of about 11.45 inches and the other end is slightly flared. The porous frit is pressed about 1/2 inch into the cut end of the shrunk tube, where about 0.05 inches to about 0.15 inches of the tip of the porous frit is typically left exposed beyond the internal tube. The about 1 inch long insert will fit inside of the flared end (up to about 1/2 inch). In an embodiment, the insert also undergoes a shrinking process as above. Alternatively, the insert is not shrunk and is a suitable size of PTFE to be inserted into the heat shrunk PTFE comprising the upper portion of the internal tube.

The base portion of the internal tube is shrunk and slightly flared as described above for the upper portion. In an embodiment, the end of the base portion that attaches to the multi-fitting housing is reinforced with additional PTFE heat shrink tubing (or other similar material) and is flared at its top end to allow insertion of the remaining about ½ inch of the insert (i.e., that part of the insert which remains outside of the bottom part of the upper portion of the internal tube). The reinforcing material aids in providing support for the internal tube at reducing union 92. The electro-chloridized reference electrode is then pressed into the reinforced end of the base portion, with the tapered end of the reference electrode being inserted into the internal tube.

In one embodiment, internal tube 82 is filled with any concentration of electrolyte solution, such as NaCl, KCl, calomel (i.e., mercury(I) chloride or $Hg_2Cl_2$), the like, and combinations thereof. In an embodiment, filling the internal tube includes separating the tube via insert and filling an inner volume of the upper portion and the base portion with electrolyte solution using a long-needled syringe. The two portions are typically filled slightly past capacity resulting in menisci. When the two portions are connected, the electrolyte solutions combine thus leaving no air bubbles inside of the connected internal tube portions. The presence of air bubbles will cause inaccurate and open-circuit measurements. Preferably, the internal tube is filled with about 0.1 N KCl. Alternatively, the electrolyte solution includes about 0.001 N to about 3.8 N KCl. In other embodiments, the EPBRE does not have an internal tube, and the external tube is filled with the electrolyte solution. That is, one tube performs the function of the combination internal tube and external tube. In alternative embodiments, a plurality of tubes may be assembled or combined concentrically to perform the described function. In further embodiments, the EPBRE includes a standard hydrogen electrode or other suitable reference electrode.

Once the assembled internal tube is slid into external tube 76 to form a tube assembly, the bottom end of the tube assembly is attached to the multi-fitting housing and the top end of the tube assembly is attached to the FTC. A small part of the external tube (e.g., about 0.05 inches to about 0.25 inches) should remain exposed beyond the respective reducing unions on either end of the external tube. Assembling the reducing unions typically involves swaging, cold pressing, etc. the unions to form a seal.

According to an embodiment, assembling the multi-fitting housing includes welding or otherwise attaching fastener 102 to the multi-fitting housing. Sealed junction 100 fits into the fastener and provides a seal for the base portion of the internal tube. High-pressure connector 80, reducing union 92, and fastener 102 are assembled to attach the base portion to the multi-fitting housing. A small part of the reference electrode protrudes into the multi-fitting housing to allow connecting the reference electrode to BNC connector 94 with a wire or other conductive material. Locking nut 96 and bolt 98 are then assembled onto the multi-fitting housing to ensure that the reference electrode remains pressed into position under operating pressure.

Assembling the top of the tube assembly includes attaching high-pressure fitting 78 to one of the ports on the FTC. In an embodiment, a reducing union, such as Part No. SS-400-R-6BT (available from, for example, Swagelok® in Solon, Ohio) is used. In alternative embodiments, any suitable fastener, coupler, etc. may be used to attach the top of the tube assembly to the FTC. In an embodiment, the distance or spatial gap between porous frit 86 (the porous frit terminates the EPBRE at the FTC end) and the band is about ¹⁄₆₄ inch or greater. Preferably, the distance is about ⅛ inch to about ½ inch and most preferably the distance is about ³⁄₁₆. Typically, the distance is about 1.5 times the diameter of the reference electrode connection end of the reference electrode and may be from about 1 to about 2 times that diameter. The end diameter preferably is about ¹⁄₁₀₀ to about 1 inch, more preferably about ⅛ inch to about ½ inch, and most preferably about ³⁄₁₆ inch. In alternative embodiments, the end may be any suitable diameter, such as from about ¹⁄₁₀₀ inch or less to about several inches or more. In each embodiment, the end diameter is related to the spatial gap and calibration (explained below) of the ORP device includes adjustments to accommodate the spatial gap.

Calibration of the ORP device includes, for example, checking the electrochemical potential of the EPBRE against a saturated potassium chloride standard half-cell. Under calibration conditions, the electrical connector normally (i.e., under operating conditions) connected to the ORP probe is connected to the EPBRE and the electrical connector normally connected to the EPBRE is connected to the standard known half-cell. Both electrodes should be immersed in a saturated potassium chloride solution. The potential difference between these two electrodes should be about 82 mV to about 92 mV if the ambient temperature is about 25° C. (preferably about 90 mV). Although the potential difference is a function of temperature, the effect of temperature is relatively small being about 2 mV from about 0° C. to about 50° C. Any significant variations from these figures typically indicate air bubbles in the electrolyte filling solution or a damaged reference electrode. A calibrated ORP device should provide a reading of zero millivolts when the connection normally used for the ORP probe is shorted to the connector normally used for the reference electrode.

Method of Detecting Process Leaks and Contamination

Figure 9:
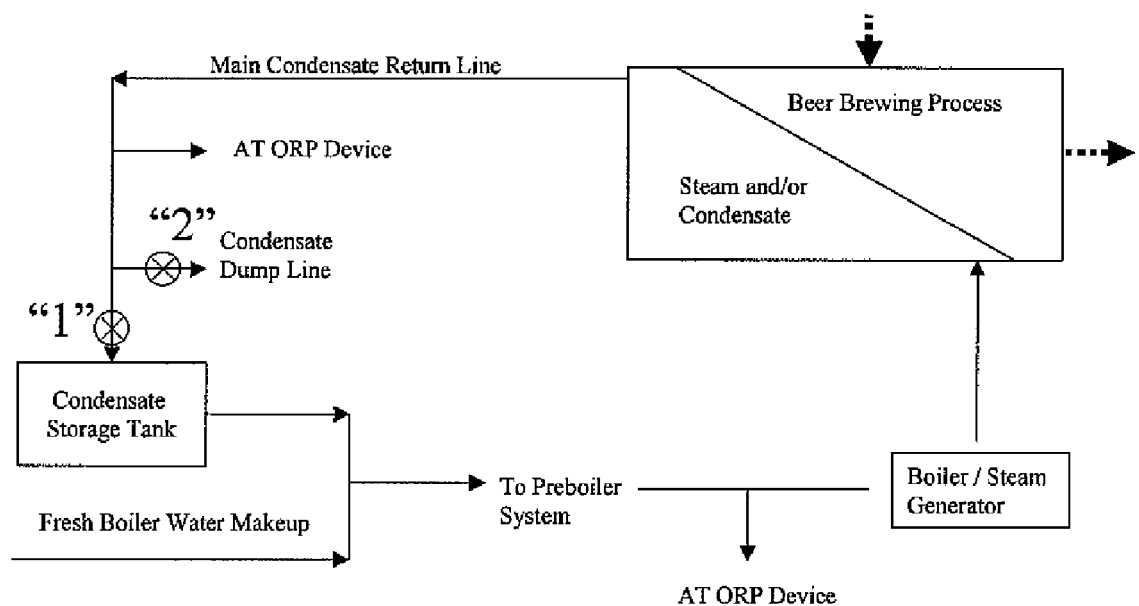
FIG. 9 shows an embodiment of the invention including two ORP devices installed in a beverage fermentation process

FIG. 9 shows an embodiment of the invention including two ORP devices installed in a beverage fermentation process. The boiler or steam generator provides a source of steam for the beer brewing process. Heat is transferred from the steam to the process via the thermodynamic connection between these two systems. Such heat transfer systems are well known in the art and further explanation is beyond the scope of this invention. It should be appreciated, however, that any boiler system or other suitable steam generating apparatus may be used with this invention. The arrow labeled "Main Condensate Return Line" directs condensate to the "Condensate Storage Tank." The condensate then combines with a source of "Fresh Boiler Water Makeup" and to the "Preboiler System" to provide additional water as needed for further steam generation.

In this embodiment, two ORP devices are installed in the system. The first ORP device is installed in the main condensate return line and the second is installed between the preboiler system and the boiler or steam generator. In one embodiment, the system includes valves, labeled "1" (valve leading to the condensate storage tank) and "2" (valve leading to the "Condensate Dump Line") in FIG. 9. The valves may either be automatically or manually adjusted (i.e., opened or closed, either completely or partially) in response to measured ORP signals.

For example, if the measured ORP signal is not within a predetermined optimum value, it may require that the condensate tank receive a smaller amount of condensate from the main condensate return line, valve "2" may be opened to release a portion of the condensate from the condensate return line via the condensate dump line. A portion or all of the condensate water may be discarded and compensated with water from a makeup water source to keep boiler feedwater ORP values within acceptable limits. Such limits typically depend upon the particular metallurgy of the system, operational parameters, etc. and are determined during a monitoring or testing period.

In an embodiment, the ORP devices monitor fluctuations in the condensate system. Such fluctuations provide information to aid in predicting possible problems in the system, such as in the full spectrum of mechanical, operational, and chemical use of the steam generating system and its components.

In an embodiment, one or more ORP devices are in contact with the boiler condensate and/or boiler feedwater. The boiler condensate may include one or both of boiler condensate return line(s) and boiler condensate storage tank.

In alternative embodiments, the method may be operated continuously, automatically, intermittently, and/or online.

The foregoing may be better understood by reference to the following examples, which are intended for illustrative purposes and are not intended to limit the scope of the invention.

Figure 10:
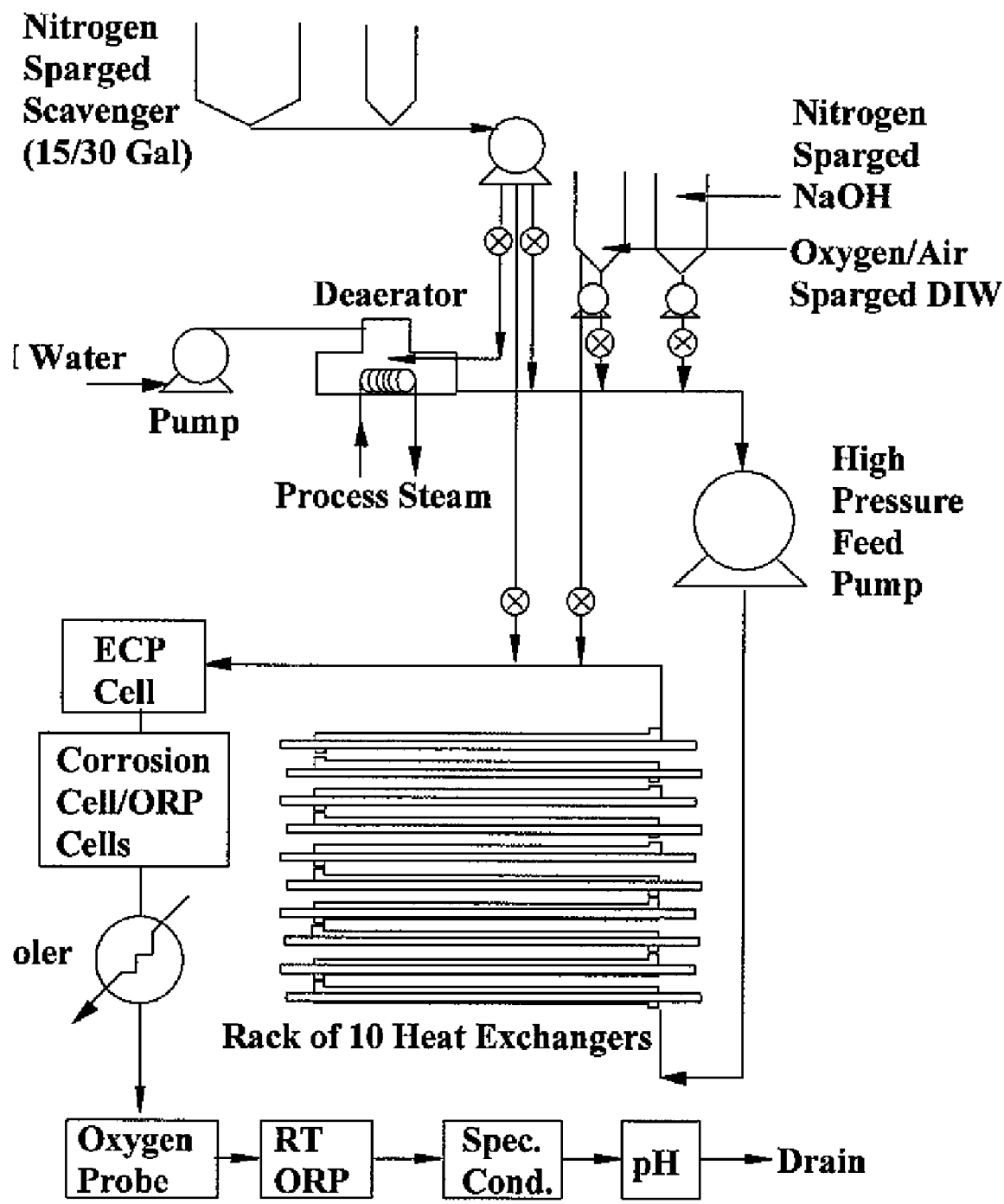
FIG. 10 shows the preboiler rig used for testing in the below example.

FIG. 10 shows the preboiler rig used for testing in the following examples. Though normally used, the corrosion cell was not in place and the electrochemical potential monitoring (ECP) cell location was replaced with a skid containing an ORP device—referred to as AT ORP™ #10 (AT ORP is a trademark of Nalco Company) in subsequent Examples and Figures. In addition, for these tests an ORP device was also positioned after the tube-in-shell heat exchanger #2 (there are typically 10 tube-in-shell heat exchangers (see FIG. 10). Data generated from that ORP probe is designated as AT ORP #2. For #2, water was extracted from the main flow path, passed through the ORP device #2, and then sent to a cooler and flow control valve prior to being dumped to drain. For the case of #10, water was then cooled, depressurized, and then some of the main water flow was sent through the low temperature analytical equipment shown in FIG. 10. The room temperature ORP device (labeled "RT ORP" in FIG. 10) was not used for these tests.

EXAMPLE 1

Figure 11:
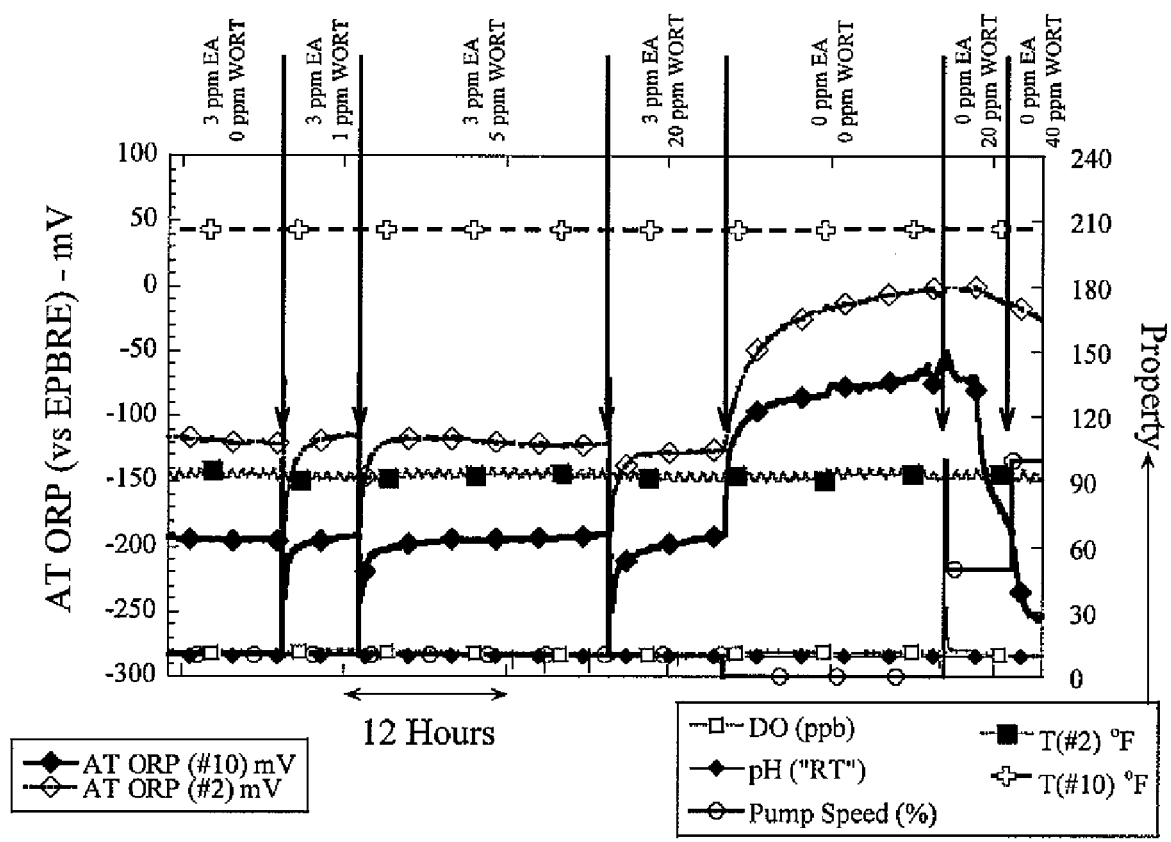
FIG. 11 shows the data traces for ORP measurements (both room temperature and at operating temperature and pressure), dissolved oxygen, temperature, and pump speed under various concentrations of erythorbic acid ("EA") baseline and wort additions.

FIG. 11 shows the data traces for ORP measurements performed for feedwater conditions (both room temperature and at operating temperature and pressure), dissolved oxygen, temperature, and pump speed under the following concentrations of erythorbic acid ("EA") baseline and wort additions: 3 ppm EA baseline with 0 ppm WORT additions; 3 ppm EA baseline with 1 ppm WORT additions; 3 ppm EA baseline with 5 ppm WORT additions; 3 ppm EA baseline with 20 ppm WORT additions; 0 ppm EA baseline with 0 ppm WORT additions; 0 ppm EA baseline with 20 ppm WORT additions; and 0 ppm EA baseline with 40 ppm WORT additions.

The 15-gallon nitrogen sparged chemical feed tank (labeled "Nitrogen Sparged Scavenger" in FIG. 10) was made up with both erythorbic acid and wort additions. For some tests, there were no erythorbic acid additions and in these cases only wort was added via the 15-gallon nitrogen sparged tank. Data from the low temperature ORP device, together with the measured at temperature and pressure ORP data is shown in FIG. 11 ("DO" refers to dissolved oxygen). Data was recorded on a Westronics Data Logger.

The chemical feed was prepared by dissolving 7.75 g erythorbic acid in a 100 ml volumetric flask prior to extracting 50 ml into the 15 Gal tank (which had been vigorously nitrogen sparged for 1 hour prior to adding the erythorbic acid solution). This resulting solution was fed after the deaerator using an LMI pump, capable of pumping at 47 ml/min at 100% pump speed and stroke. The LMI pump stroke was set to 50% and the pump speed was controlled as shown in the graph of FIG. 11. At 10% speed, the eyrthorbic acid was fed into the PBS feedwater sample stream (500 ml/min) to achieve an equivalent concentration of 3 ppm of EA actives. Supplemental caustic was added via the tank labeled "Nitrogen Sparged NaOH" in FIG. 10. This caustic makeup tank had about 12.4 g 50% NaOH in 20-liters of water. The pH in the system was controlled to about 9.2 (at 77° F.).

The temperature in the "Rack of 10 Heat Exchangers" (as shown in FIG. 10) was set as follows:

| Heater # | Kilo Watt Heat Input (kW) |
|---|---|
| 1 | 0.3 |
| 2 | 0.3 |
| 3 | 0.3 |
| 4 | 0.3 |
| 5 | 0.3 |
| 6 | Temperature Controlled to 160° F. (71° C.) |
| 7 | 0.25 |
| 8 | 0.25 |
| 9 | 0.25 |
| 10 | Temperature Controlled to 223° F. (106° C.) |

This setup caused the temperature of AT ORP cell #2 and AT ORP cell #10, to remain essentially constant (see FIG. 11). Due to PID control of the water temperature prior to AT ORP cell #10, it displays less variation.

Raw material (for wort preparation) was purchased as a hopped malt extract containing malted barley, hops, hop extract, and water. A solution of the malt syrup (raw material) was made and boiled for 2 hrs in an Erlenmeyer flask and capped. Any water lost due to evaporation was added back to the solution slowly during the boiling process, so as not to upset the boiling process. 35.8 g wort raw material was added to make up the water solution to the 500 ml mark. The solution was brought to boiling and slowly stirred throughout the 2 hr boiling process. After boiling, the product was capped and cooled in a refrigerator prior to being used in the PBS rig. The amount of such wort solution added to the 15-gallon makeup tank was adjusted for each test to provide the appropriate concentration for the pump speeds shown in FIG. 11.

It can be seen from FIG. 11 that the at temperature and pressure ORP drops quite precipitously on addition of the wort. It appears the −200 mV ORP space (for AT ORP #10) with EA additions is acting as a type of oxidation-reduction buffer in this particular system. FIG. 11 shows quite clearly that wort is detected as it is added by itself to the preboiler system. Also of important note is that during the short tests run to date, the lower temperature AT ORP #2 does not respond the same way as the higher temperature AT ORP #10. The AT ORP #10 shows a much larger drop in its measured ORP as compared to AT ORP #2, as summarized in the table below:

| ppm WORT | AT ORP #2 | AT ORP #10 |
|---|---|---|
| 0 | 0 | −65 |
| 20 | −12 | −187 |
| 40 | −24 | −256 |

Figure 12:
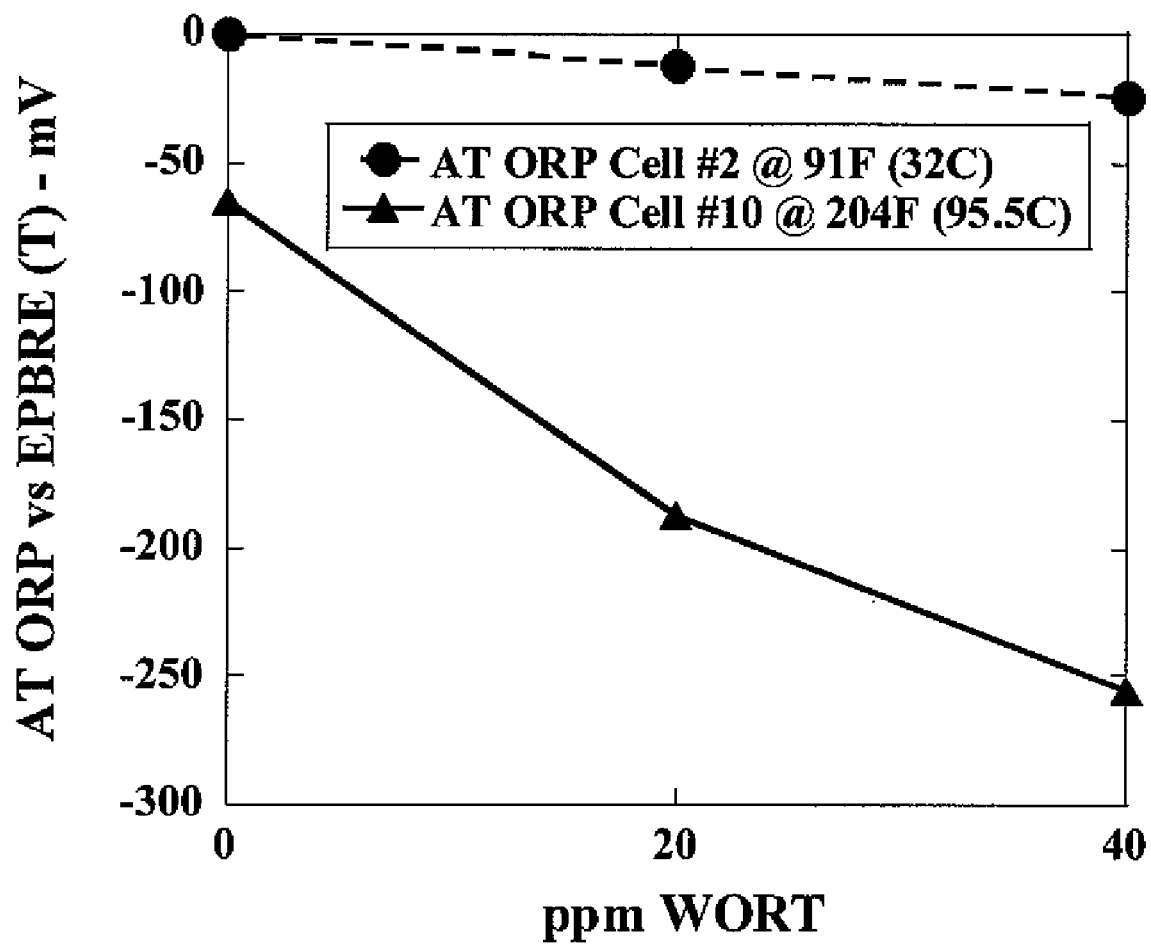
FIG. 12 illustrates the at temperature and pressure ORP response to wort in the system.

FIG. 12 further illustrates the at temperature and pressure ORP response to wort in the system. It can be seen that the higher temperature ORP signal responds significantly to increases in wort concentration, whereas the lower temperature ORP signal displays much reduced sensitivity.

It should be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The invention claimed is:

1. A method for detecting contamination of a boiler condensate and/or a boiler feedwater in an industrial process, the method comprising:
   (a) measuring an oxidation reduction potential at one or more locations with one or more devices in contact with the boiler condensate and/or the boiler feedwater of the industrial process at operating temperature and pressure ("ORP device"); and
   (b) triggering an alarm or other indicator if the measured oxidation reduction potential is not within an optimum range.

2. The method of claim 1, wherein the industrial process is a fermentation process.

3. The method of claim 2, wherein the fermentation process is a beer making process or a distillation process.

4. The method of claim 1, including converting the measured oxidation reduction potential into an input electrical signal capable of being transmitted to a controller and transmitting the input electrical signal to the controller.

5. The method of claim 1, wherein the controller is operable to: (i) receive the transmitted input electrical signal; (ii) convert the received electrical signal into an input numerical value; (iii) analyze the input numerical value; (iv) generate an output numerical value: (v) convert the output numerical value into an output electrical signal; and (vi) transmit the output electrical signal.

6. The method of claim 4, including determining if the input numerical value is within the optimum range, and if the input numerical value is outside of the optimum range, the transmitted output electrical signal corresponding to the generated output numerical value triggering the alarm.

7. The method of claim 1, wherein the boiler condensate includes a boiler condensate return line and/or a boiler condensate storage tank.

8. The method of claim 1, wherein the one or more installed ORP devices are in contact with the boiler condensate and/or the boiler feedwater.

9. The method of claim 1, including transmitting the input electrical signal and/or the output electrical signal wirelessly.

10. The method of claim 1, wherein the optimum range is user-defined.

11. The method of claim 1, including operating the method continuously, automatically, and/or online.

12. The method of claim 1, including operating the method intermittently.

13. The method of claim 1, including a mechanism to open or close one or more valves associated with the boiler condensate and/or a boiler feedwater.

14. The method of claim 1, including operating the method over a network.

15. A digital storage medium having computer-executable instructions stored thereon, the instructions operable to execute the method of claim 1.

16. A system for detecting contamination of boiler condensate and/or boiler feedwater in a beverage fermentation process, the system comprising: a boiler or other steam generator at operating temperature and pressure; a beverage fermentor; an interface that forms a thermodynamic connection between the beverage fermentor and a steam and/or condensate stream derived from said boiler or steam generator; a condensate return line; a condensate storage tank; a condensate dump valve; a boiler makeup water source; and one or more at temperature and pressure oxidation reduction potential measuring devices.

* * * * *